United States Patent [19]

Madison et al.

[11] Patent Number: 5,466,396
[45] Date of Patent: Nov. 14, 1995

[54] ISETHIONATE ESTERS OF ALKYL ALKOXY CARBOXYLIC ACID

[75] Inventors: Stephen A. Madison, New City; Michael Massaro, Congers, both of N.Y.; Gail B. Rattinger, Teaneck; Christine Wenzel, Ridgewood, both of N.J.

[73] Assignee: Lever Brothers Company, New York, N.Y.

[21] Appl. No.: 154,897

[22] Filed: Nov. 19, 1993

[51] Int. Cl.$^6$ .............................. C11D 1/28; C11D 3/50; C11D 3/20
[52] U.S. Cl. .......................... 252/557; 252/538; 252/554; 252/535; 252/549; 560/183; 560/186
[58] Field of Search .................... 560/183, 186; 252/557, 538, 554, 535, 549

[56] References Cited

U.S. PATENT DOCUMENTS

| | | | |
|---|---|---|---|
| 5,230,823 | 7/1993 | Wise et al. | 252/174.21 |
| 5,232,633 | 8/1993 | Ilardi et al. | 252/554 |
| 5,282,987 | 2/1994 | Balzer et al. | 252/34 |
| 5,393,466 | 2/1995 | Ilardi et al. | 252/549 |

FOREIGN PATENT DOCUMENTS

| | | |
|---|---|---|
| 0499229 | 2/1992 | European Pat. Off. . |
| 140079 | 6/1993 | Japan . |
| 209910 | 1/1987 | United Kingdom . |

*Primary Examiner*—Paul Lieberman
*Assistant Examiner*—Michael P. Tierney
*Attorney, Agent, or Firm*—Ronald A. Koatz

[57] ABSTRACT

The present invention is directed to novel compounds having the formula:

$$R(OC_mH_{m+1})_nOCH_2\overset{O}{\underset{\|}{C}}-\overset{X}{\underset{|}{O}}CH_2CH_2SO_3^-Na^+$$

wherein
R is a $C_8$–$C_{24}$ substituted or unsubstituted alkyl or alkenyl group;
m is 1 to 3;
n is 1 to 5; and
x is hydrogen or a $C_1$ to $C_3$ hydrocarbon.

The compounds are mild and good foaming compounds which can be used in both personal washing bars and liquids.

3 Claims, No Drawings

ISETHIONATE ESTERS OF ALKYL ALKOXY CARBOXYLIC ACID

BACKGROUND OF THE INVENTION

1. Field of the Invention

The present invention relates to isethionate esters of alkyl alkoxy carboxylic acid as well as to compositions comprising the novel isethionate esters.

2. Prior Art

Alkyl alkoxy (e.g., alkyl ethoxy) carboxylic acids such as $R(OCH_2CH_2)_nOCH_2COOH$, wherein R is $C_8$–$C_{18}$ and n is, for example, 2, are known. Similarly, alkali metal isethionates such as $HOCH_2CH_2SO_3^-Na^+$ are also known. The ester reaction product of these two compounds, however, is neither taught nor suggested by the art.

EP 0,499,229 discloses compounds which are amides of the alkyl alkoxy carboxylic acid rather than esters. That is, an acid reacts with $NH_2CH_2CH_2SO_3^-Na^+$ instead of $HOCH_2CH_2SO_3^-Na^+$.

SUMMARY OF THE INVENTION

Unexpectedly, applicants have now found a new class of compounds which are esters (e.g., isethionate esters) of alkyl alkoxycarboxylic acids. These novel esters are very mild and foam well and may be used in both personal washing bars and liquids. In one embodiment of the invention, it has also been found that, when an excess of the fatty acid precursor is neutralized, the mixture of (a) isethionate esters of alkyl alkoxycarboxylic acid and (b) neutralized excess fatty acid compound functions to further enhance detergency.

More specifically, the present invention relates to isethionate esters of alkyl alkoxycarboxylic acids having the formula:

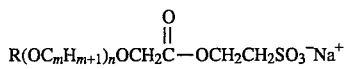

where

R is $C_8$–$C_{24}$, preferably $C_{10}$–$C_{18}$ substituted or unsubstituted alkyl or alkenyl;

m is 1 to 3, preferably 1 to 2; and n is 1 to 5, preferably 1 to 2.

Such compounds are mild, good foaming surfactants.

Among the compositions in which these mild surfactants may be used include heavy and light duty liquid detergents, detergent bar compositions and personal product compositions (e.g., shampoos, facial cleansers, foam baths etc.).

DETAILED DESCRIPTION OF THE INVENTION

The present invention relates to isethionate esters of alkyl alkoxycarboxylic acids having the formula:

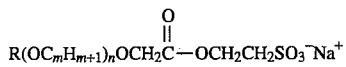

wherein

R is $C_8$ to $C_{24}$ substituted or unsubstituted alkyl or alkenyl group, preferably $C_{10}$–$C_{18}$;

m is 1 to 3, preferably 1 to 2; and n is 1 to 8, preferably 1 to 2.

In one embodiment of the invention, the alpha carbon on the isethionate (i.e., the isethionate moiety of the molecule) may be branched with a $C_1$ to $C_3$ hydrocarbon group.

These molecules were found to be comparable to the alkoxylated isethionates of U.S. Ser. No. 08/045,951 to Ilardi et al., filed Apr. 12, 1993.

Moreover, the process offers an alternative route (i.e., because alkoxylation units are on fatty acid precursor rather than the isethionate precursor) which may be preferable with respect to ease of commercial preparation.

Preparation

The isethionate esters of alkyl alkoxycarboxylic acid may be prepared as described below:

The isethionate esters of alkyl alkoxycarboxylic acid may be prepared via direct esterification of a fatty acid and an isethionate (i.e., directly esterified fatty acid isethionate or DEFI).

In general, a glass reactor (e.g., consisting of a 500 mL cylindrical bottom piece and a 4-neck glass top piece which is fitted with a thermocouple), a mechanical stirrer, a nitrogen gas inlet tube and distillation apparatus, are charged with an alkyl alkoxycarboxylic acid, sodium isethionate (that is pre-dissolved in water), and ZnO (zinc oxide catalyzes reaction). Under standard conditions, the molar ratio of isethionate to fatty acid is 1:1.35 and ZnO represent 0.1118% of reactant weight. The vessel is heated using a heating mantle connected to a temperature controlled heating unit. At 45° C., the nitrogen sparging is initiated (generally 40 cc/min), and the temperature stabilizes at about 103° C. until the water distills off with a small amount of the alkoxy fatty acid. Once the water is removed, the reaction is generally heated to 220°–240° C. for about 90 minutes. The reaction is allowed to cool to room temperature to afford a brown viscous liquid. The semi-solid state is due to the excess alkoxy fatty acid. Acetone washing removes the excess alkoxy fatty acid, affording a solid.

In order to prepare the sodium salt of alkyl alkoxycarboxylate, alkyl alkoxy carboxylic acid and distilled water are placed in a 1 L Erlenmeyer flask, equipped with a magnetic stir bar, pH electrode, on a magnetic stir plate. 1N NaOH is added to adjust the pH from 3 to 9.19. The clear solution is lyophilized, affording an off-white solid.

Neutralization of fatty acid precursor will occur only if there is an excess stochiometric amount of fatty acid reactant or if it is post-dosed after the reaction is complete (in the above description, the neutralized fatty acid was prepared by post-dosing). Whether prepared by post-dosing or because there is excess starting reactant, the neutralized carboxylic acid offers a number of advantages.

First, the neutralized carboxylic acid is an anionic surfactant compared to the unneutralized acid which is not. In general, anionics are much better foamers and thus the neutralized compound enhances foaming.

Second, anionic compounds are solid or semisolid at room temperature rather than liquid. This is greatly beneficial in the formation of a bar product.

Finally, the neutralized carboxylic acid functions together with isethionate to produce a sort of two-surfactant system.

Compositions

The compounds of the invention may be used in any cleaning or cleansing composition as may be known to those skilled in the art. For example, the compound may be used in fabric washing compositions (e.g., liquid fabric detergents) or in various personal washing compositions such as toilet bars, hand or body cleansers, shampoos, as well as other compositions where mild surfactants might be desired (e.g., light duty liquid dishwashing compositions).

To the extent that the surfactants may be used in any cleaning or cleansing composition known to those skilled in the art, it will be understood by those skilled in the art that the surfactants may be used in combination with one or more cosurfactants in binary active systems, ternary active systems etc. Depending on the compositions, the active may comprise the majority of the active system (if more than one active is required) or it may comprise less than the majority of the active system.

In one embodiment of the invention, the isethionate esters of alkyl alkoxycarboxylic acid of the invention may be used, for example, in a toilet bar (i.e. detergent and/or soap bar) formulation.

Typical toilet bar compositions are those comprising fatty acid soaps used in combination with a detergent other than fatty acid soap and free fatty acids. It should be noted that the composition may comprise no fatty acid soap and may be based on actives other than fatty acid soap. Mildness improving salts, such as alkali metal salt or isethionate, are also typically added. In addition other ingredients, such as germicides, perfumes, colorants, pigments, suds-boosting salts and anti-mushing agents may also be added.

Fatty acid soaps are typically alkali metal or alkanol ammonium salts of aliphatic alkane or alkene monocarboxylic acids. Sodium, potassium, mono-, di- and tri-ethanol ammonium cations, or combinations thereof, are suitable for purposes of the invention. The soaps are well known alkali metal salts of natural or synthetic aliphatic (alkanoic or alkenoic) acids having about 8 to 22 carbons, preferably 12 to about 18 carbons. They may be described as alkali metal carboxylates or acrylic hydrocarbons having about 12 to 22 carbons.

Examples of soap which may be used may be found in U.S. Pat. No. 4,695,395 to Caswell et al. and U.S. Pat. No. 4,260,507 (Barrett), both of which are incorporated herein by reference.

In a soap-based bar, fatty acid soaps will generally comprise greater than 25% of the composition, generally from 30–95%. Preferably, the amount of soap will range from 40% to 70% by weight of the composition.

In a bar based on other actives, soap may comprise 0–50% by weight. In general $C_8$ to $C_{24}$ fatty acid comprises 5–60% of the composition.

The compositions will also generally comprise a non-soap detergent which is generally chosen from anionic, nonionic, cationic, zwitterionic or amphoteric synthetic detergent materials or mixtures there of. These surfactants are all well known in the art and are described, for example, in U.S. Pat. Nos. 4,695,395 and 4,260,507 discussed above. One preferred non-soap anionic is a $C_8$–$C_{22}$ alkyl isethionate. These esters may be prepared by the reaction between alkali metal isethionate and mixed aliphatic fatty acids having from 8 to 22 carbons. The non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 15% of the compositions.

A preferred mildness improving salt which may be added to soap compositions is a simple unsubstituted sodium isethionate. This may be present as 0.1 to 50% of the composition, preferably .5% to 25%, more preferably 2% to about 15% by weight. Other mildness co-actives which may be used include betaine compounds or ether sulfates. These also may be present at 0.1 to 50% of the composition, preferably 0.5% to 25%.

The sulfonated ester surfactant may comprise .01 to 45% by weight of the composition (as the monoester), preferably 25% to 40%, and .01% of the composition (as the diester), preferably .01% to 5%.

Other optional ingredients which may be present in soap bar compositions are moisturizers such as glycerin, propylene glycol, sorbitol, polyethylene glycol, ethoxylated or methoxylated ether of methyl glucose etc.; water-soluble polymers such as collagens, modified cellulases (such as Polymer JR®), guar gums and polyacrylates; sequestering agents such as citrate, and emollients such as silicones or mineral oil. Another useful set of ingredients are various co-surfactants and non-soap detergents.

A typical toilet bar based on alkyl ethoxy carboxy isethionate is as follows: (all percentages by weight).

| | |
|---|---|
| Sodium Cocoyloxy (2.5 EO) acetyl isethionate | 50% |
| Stearic Acid | 20% |
| Sodium Coco (2.5 EO) carboxylate | 7% |
| 82/18 Soap* | 4% |
| Sodium Isethionate | 4% |
| Coconut Fatty Acid | 3% |
| Sodium Stearate | 3% |
| Perfume | 1% |
| Water, preservatives & colorants | 5% |
| Organic salts and/or inorganic salts of the various ingredients | 3% |

*Ratio of coconut fatty acid to tallow fatty acid

In a second embodiment of the invention, the isethionate esters of alkyl alkoxy carboxylic acids of the invention may be present in a facial or body cleaning composition. Examples of such cleaning compositions are described, for example, in U.S. Pat. No. 4,812,253 to Small et al. and U.S. Pat. No. 4,526,710 to Fujisawa, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener (e.g., magnesium aluminum silicate, carbopol), conditioners, water soluble polymers (e.g., carboxymethylcellulose), dyes, hydrotropes brighteners, perfumes and germicides.

The fatty acid soaps used are such as those described above in uses in detergent bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695, 395 mentioned above, or in U.S. Pat. No. 4,854,333 to Inman et al., hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add non-occlusive hygroscopic substances to the stratum corneum which will retain water, and make this water available to the st stratum corneum to alter its physical properties and produce a cosmetically desirable effect. Non-occlusive moisturizers also function by improving the lubricity of the skin.

Both occlusive and non-occlusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/-propoxylated ethers of lanolin alcohol (e.g., Solulan-75).

Preferred moisturizers are coco and tallow fatty acids. Some other preferred moisturizers are the non-occlusive liquid water soluble polyols and the essential amino acid compounds found naturally in the skin.

Other preferred non-occlusive moisturizers are compounds found to be naturally occurring in the stratum corneum of the skin, such as sodium pyrrolidone carboxylic acid, lactic acid, urea, L-proline, guanidine and pyrrolidone. Examples of other non-occlusive moisturizers include hexadecyl, myristyl, isodecyl or isopropyl esters of adipic, lactic oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseen oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—a Critical Evaluation," by J. Mausner, Cosmetics & Toiletries, May, 1981, incorporated herein by reference.

The polymeric skin feel and mildness aids useful in the present invention are the cationic, anionic, amphoteric, and the nonionic polymers used in the cosmetic field. Reduced skin irritation benefits as measured by patch testing of cationic and nonionic types of polymers are set out in "Polymer JR for Skin Care" bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, Merquats 100 and 550, made by Merck & Co., Inc.; Jaguar C-14-S made by Stein Hall; Mirapol A15 made by Miranol Chemical Company, Inc.; and Galactasol 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Crop. A preferred nonionic hydroxypropyl guar gum material is Jaguar® HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1–5% of the composition. There is reason to believe that the positively charged cationic polymers can bind with negatively charges sites on the skin to provide a soft skin feel after use. Not to be bound by any theory, it is believed t hat the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok® 300 and 400 made by Staley, Inc.

A more complete list of cationic polymers useful in the present invention is described in U.S. Pat. No. 4,438,095, to Grollier/Allec, issued Mar. 20, 1984, incorporated herein by reference. Some of the more preferred cationics are listed in Column 3, Section 2; Column 5, Section 8; Column 8, Section 10; and Column 9, lines 10–15 of the Grollier/Allec patent, incorporated herein by reference.

In a third embodiment of the invention, the surfactant of the invention may be used, for example, in a shampoo composition. Examples of such compositions are described in U.S. Pat. No. 4,854,333, to Inman and U.S. Pat. No. 4,526,710 to Fujisawa, both of which are hereby incorporated by reference.

The shampoo compositions which may be used typically comprise a surfactant selected from any one of a wide variety of surfactants known in the art (such as those described in U.S. Pat. No. 4,854,333, incorporated herein by reference). The shampoo compositions may additionally comprise a compound considered useful for treating dandruff, e.g., selenium sulfide.

The compositions all may also optionally comprise a suspending agent, for example any of several acyl derivative materials or mixtures thereof. Among these are ethylene glycol esters of fatty acids having 16 to 22 carbons. Preferred suspending agents include ethylene glycol stearates, both mono- and distearate. Preferred alkanol amides are stearic monoethanolamide, stearicdiethanolamide and stearic monoisopropanolamide. Still other long chain acyl derivatives include long chain esters of long chain fatty acids (e.g., stearyl stearate, cetyl palmitate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another agent used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucoronate in the molar ratio of 2.8:2.0:2.0. The polysaccharide is partially acetylated with 4.7% acetyl. Supplemental information on these agents is found in Whistler, Roy L. (Editor), *Industrial Gums—Polysaccharides and Their Derivatives* New York: Academic Press, 1973. Kelco, a Division of Merck & Co., Inc., offers xanthan gum as Keltrol®. A particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%, of the compositions. Magnesium aluminum silicate occurs naturally in such smectite minerals as colerainite, saponite and sapphire. Refined magnesium aluminum silicates useful herein are readily available, for example as veegum, manufactured by R. T. Vanderbilt Company, Inc. Mixtures of suspending agents are also suitable for use in the compositions of this invention.

Other useful thickening agents are the cross-linked polyacrylates such as those manufactured by B. F. Goodrich and sold under the Carbopol® tradename.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials. Other materials include alginates, polyacrylic acids, polyethylene glycol and starches, among many others. The nonionic polymers are discussed in detail in *Industrial Gums*, edited by Roy L. Whistler, Academic Press, inc., 1973, and *Handbook of Water-Soluble Gums and Resins*, edited by Robert L. Davidson, McGraw-Hill, Inc., 1980. Both of these books in their entirety are incorporated herein by references.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present composition is a nonvolatile silicone fluid.

The nonvolatile silicone fluid may be either a polyalkyl siloxane, a polyaryl siloxane, a polyalkylaryl siloxane or a polyether siloxane copolymer and is present at a level of from about 0.1% to about 10.%, preferably from about 0.5% to about 5.0%. Mixtures of these fluids may also be used and are preferred in certain executions. The dispersed silicone particles should also be insoluble in the shampoo matrix. This is the maning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric company as the Viscasil series and from Dow Corning as the Dow Corning 200 series. The siloxane viscosity can be measured by means of a glass capillary viscometer as set forth in Dow Corning Corporate Test Method CTM0004, Jul. 20, 1970. Preferably the viscosity of these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 4,364,837, Pader; and British Patent 849,433, Wooston. All of these patents are incorporated herein by reference. Also incorporated herein by reference is silicon compounds, distributed by Petrarch Systems, Inc., 1984. This reference provides a very good listing of suitable silicone materials.

Another silicone material useful is silicone gum. Silicone gums are described Petrarch and others including U.S. Pat. No. 4,152,416, May 1, 1979, Spitzer, et al., and Noll, *Chemistry and Technology of Silicones*, New York, Academic Press, 1968. Useful silicone gums are also described in General Electric Silicone Rubber Product Data Sheets SE 30, SE 33, SE 54 and SE 76. All of these references are incorporated herein by reference. "Silicone gum" materials denote high molecular weight polysdiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammoniumchloride, and di(partially hydrogenated tallow) dimethylammonium chloride; menthol; thickeners and viscosity modifiers, such as block polymers of ethylene oxide and propylene oxide such as Pluronic F88 offered by BaSa Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes and sequestering agents, such as disodium ethylenediamine tetraacetate. Such agents generally are used individually at a level of from about 0.01% to about 10%, preferably from about 0.5% to about 5.0%, of the composition.

A typical shampoo composition might comprise (percentages of weight):

(1) 5–15% isethionate ester of alkyl alkoxycarboxylic acid (2) 0–10% anionic coactive (3) 0–10% amphoteric coactive (4) 0–5% lauramide MEA (5) 0–5% thickener (6) 0–2% fragrance (7) 0–1% preservative: and (8) remainder water In a fourth embodiment of the invention, the surfactant of the invention may be used in a conditioner composition such as is taught and described in U.S. Pat. No. 4,913,828 to Caswell et al. which is hereby incorporated by reference.

More particularly, conditioner compositions are those containing a conditioning agent (e.g., alkylamine compounds) such as those described in U.S. Pat. No. 4,913,828.

In a fifth embodiment of the invention, the surfactant may be used in a cosmetic composition, such as is taught and is described in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxy methyl cellulose; anionic polymers such as carboxy vinyl polymers, for example, Carbomer 940 and 941; nonionic cellulose materials, such as methyl cellulose and hydroxy propyl methyl cellulose; cationic cellulose materials, such as Polymer JR 400; cationic gum materials, such as Jaguar C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1, 3-diol, phenoxyethanol, dibromodicyanobutane, formalin and Tricolsan. The amount of chemical preservative optionally to be incorporated in the composition according to the invention will generally be from 0.05 to 5%, preferably from 0.01 to 2% by weight, the amount chosen being sufficient to arrest microbial poliferation.

(ii) Water activity depressants, such as glycerol, propylene glycol, sorbitol, sugars and salts, for examples alkali metal halides, sulfates and carboxylates. When employing a water activity depressant, a sufficient amount should be incorporated in the composition according to the invention to reduce the water activity from 1 to <0.9, preferably to <0.85 and most preferably <0.8, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1.3 diol, docosan-2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmirate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichloromethane, dichlorodifluoromethane, dichlorotetrafluoromethane, monochlorodifluoromethane, trichlorotrifluoromethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulfoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fuller's earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sun-screening agents, such as those described in U.S. Pat. No. 4,919,934 to Deckner et al. hereby incorporated by reference, may also be used in the cosmetic compositions of the invention.

Such agents include, for example, p-aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphthloic acid and its salts, hydroxy diphenylsulfonates, coumarin derivatives, diazones, quinine salts, quinoline derivatives, hydroxy or methoxy substituted benzophenones, uric or vilouric acid, tannic acid and its derivatives, hydroquinone, and benzophenones.

In a sixth embodiment of the invention, the molecule of the invention may be used in a light duty liquid detergent composition such as those taught in U.S. Pat. No. 4,671,894 to Lamb et al., and U.S. Pat. No. 4,368,146 to Aronson et al. all of which are hereby incorporated by reference into the subject application.

Generally such compositions comprise a mixture of sulfate and sulfonate anionic surfactants together with a suds stabilizing agent. These compositions may also comprise nonionic surfactants designed to reduce the level of non-performing ingredients such as solvents and hydrotropes and zwitterionic surfactants for providing enhanced grease and particulate soil removal performance.

Among other ingredients which may also be used in such compositions are opacifiers (e.g., ethylene glycol distearate), thickeners (e.g., guar gum), antibacterial agents, anti-tarnish agents, heavy metal chelators (e.g., ETDA), perfumes and dyes.

While various compositions are described above, these should not be understood to be limiting as to what other personal product compositions may be used since other compositions which may be known to those of ordinary skill in the art are also contemplated by this invention.

In addition, the surfactants of the invention may also be used in cleansing or detergent compositions such as heavy duty liquids (generally enzyme containing) or detergent powders. Examples of liquid detergent compositions are described in U.S. Pat. No. 4,959,179 to Aronson et al. hereby incorporated by reference into the subject application; and examples of powdered detergent compositions are described in U.S. Pat. No. 4,929,379 to Oldenburg et al. hereby incorporated by reference into the subject application.

The liquid detergent compositions of the invention may be built or unbuilt and may be aqueous or non-aqueous. The compositions generally comprise about 5%–70% by weight of a detergent active material an from 0% to 50% of a builder. The liquid detergent compositions of the invention may further comprise an amount of electrolyte (defined as any water-soluble salt) whose quantity depends on whether or not the composition is structured. By structured is meant the formation of a lamellar phase sufficient to endow solid suspending capability.

More particularly, while no electrolyte is required for a non-structured, non-suspending composition, at least 1%, more preferably at least 5% by weight and most preferably at least 15% by weight electrolyte is used. The formation of a lamellar phase can be detected by means well known to those skilled in the art.

The water-soluble electrolyte salt may be a detergency builder, such as the inorganic salt sodium tripolyphosphate or it may be a non-functional electrolyte such as sodium sulfate or chloride. Preferably, whatever builder is used in the composition comprises all or part of the electrolyte.

The liquid detergent composition generally further comprises enzymes such as proteases, lipases, amylases and cellulases which, when present, may be used in amounts from about 0.01 to 5% of the compositions. Stabilizers or stabilizer systems may be used in conjunction with enzymes and generally comprise from about 0.1 to 15% by weight of the composition.

The enzyme stabilization system may comprise calcium ion, boric acid, propylene glycol and/or short chain carboxylic acids. The composition preferably contains from about 0.01 to about 50, preferably from about 0.1 to about 30, more preferably from about 1 to about 20 millimoles of calcium ion per liter.

When calcium ion is used, the level of calcium ion should be selected so that there is always some minimum level available for the enzyme after allowing for complexation with builders, etc., in the composition. Any water-soluble calcium salt can be used as the source of calcium ion, including calcium chloride, calcium formate, calcium acetate and calcium propionate. A small amount of calcium ion, generally from about 0.05 to about 2.5 millimoles per liter, is often also present in the composition due to calcium in the enzyme slurry and formula water.

Another enzyme stabilizer which may be used is propionic acid or a propionic acid slat capable of forming propionic acid. When used, this stabilizer may be used in an amount from about 0.1% to about 15% by weight of the composition.

Another preferred enzyme stabilizer is polyols containing only carbon, hydrogen and oxygen atoms. They preferably contain from 2 to 6 carbon atoms and from 2 to 6 hydroxy groups. Examples include propylene glycol (especially 1,2 propane diol which is preferred), ethylene glycol, glycerol, sorbitol, mannitol and glucose. The polyol generally represents from about 0.5% to about 15%, preferably from about 1.0% to about 8% by weight of the composition.

The composition herein may also optionally contain from about 0.25% to about 5%, most preferably from about 0.5% to about 3% by weight of boric acid. The boric acid may be, but is preferably not, formed by a compound capable of forming boric acid in the composition. Boric acid is preferred, although other compounds such as boric oxide, borax and other alkali metal borates (e.g., sodium ortho-, meta- and pyroborate an sodium pentaborate) are suitable. Substituted boric acids (e.g., phenyl boronic acid, butane boronic acid and a p-bromo phenyl boronic acid) can also be used in place of boric acid.

One especially preferred stabilization system is a polyol in combination with boric acid. Preferably, the weight ratio of polyol to boric acid added is at least 1, more preferably at least about 1.3.

With regard to the detergent active, the detergent active material may be an alkali metal or alkanolamine soap or a 10 to 24 carbon atom fatty acid, including polymerized fatty acids, or an anionic, a nonionic, cationic, zwitterionic or amphoteric synthetic detergent material, or mixtures of any of these.

Examples of the anionic synthetic detergents are salts (including sodium, potassium, ammonium and substituted ammonium salts) such as mono-, di- and triethanolamine salts of 9 to 20 carbon alkylbenzenesulfonates, 8 to 22 carbon primary or secondary alkanesulfonates, 8 to 24 carbon olefinsulfonates, sulfonated polycarboxylic acids prepared by sulfonation of the pyrolyzed product of alkaline earth metal citrates, e.g., as described in British patent specification, 1,082,179, 8 to 22 carbon alkylsulfates, 8 to 24 carbon alkylpolyglycol-ether-sulphates, -carboxylates and phosphates (containing up to 10 moles of ethylene oxide); further examples are described in "Surface Active Agents and Detergents" (vol. I and II) by Schwartz, Ferry and Bergh. Any suitable anionic may be used and the examples are not intended to be limiting in any way.

Examples of nonionic synthetic detergents which may be used with the invention are the condensation products of ethylene oxide, propylene oxide and/or butylene oxide with 8 to 18 carbon alkylphenols, 8 to 18 carbon fatty acid amides; further examples of nonionics include tertiary amine oxides with 8 to 18 carbon alkyl chain and two 1 to 3 carbon alkyl chains. The above reference also describes further examples of nonionics.

The average number of moles of ethylene oxide and/or propylene oxide present in the above nonionics varies from 1–30; mixtures of various nonionics, including mixtures of nonionics with a lower and a higher degree of alkoxylation, may also be used.

Examples of cationic detergents which may be used are the quaternary ammonium compounds such as alkyldimethylammonium halogenides.

Examples of amphoteric or zwitterionic detergents which may be used with the invention are N-alkylamide acids, sulfobetaines, condensation products of fatty acids with protein hydrolysates; but owing to their relatively high costs they are usually used in combination with an anionic or a nonionic detergent. Mixtures of the various types of active detergents may also be used, and preference is given to mixtures of an anionic and a nonionic detergent active. Soaps (in the form of their sodium, potassium and substituted ammonium salts) of fatty acids may also be used, preferably in conjunction with an anionic and/or nonionic synthetic detergent.

Builders which can be used according to this invention include conventional alkaline detergency builders, inorganic or organic, which can be used at levels from 0% to about 50% by weight of the composition, preferably from 1% to about 20% by weight, most preferably from 2% to about 8%.

Examples of suitable inorganic alkaline detergency builders are water-soluble alkali metal phosphates, polyphosphate, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetraacetates, nitrilotriacetates and N-(2 hydroxyethyl)-nitrilodiacetates; (2) water-soluble salts of phytic acid, e.g., sodium and potassium phytates (see U.S. Pat. No. 2,379,942); (3) water-soluble polyphosphonates, including specifically, sodium, potassium and lithium salts of ethane-1-hydroxy-1, 1 diphosphonic acid; sodium, potassium and lithium salts of methylene diphosphonic acid; and sodium, potassium and lithium salts of ethane-1,1,2-triphosphonic acid. Other examples include the alkali metal salts of ethane -2-carboxy-1,1-diphosphonic acid hydroxymethanediphosphonic acid, carboxylidiphosphonic acid, ethane- 1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water soluble salts of polycarboxylate polymers and copolymers as described in U.S. Pat. No. 3,308,067.

In addition, polycarboxylate builders can be used satisfactorily, including water-soluble salts of mettitic acid, citric acid, and carboxymethyloxysuccinic acid and salts of polymers of itaconic acid and maleic acid. Other polycarboxylate builders include DPA (dipicolinic acid) and ODS (oxydisuccinic acid). Certain zeolites or aluminosilicates can be used. One such aluminosilicate which is useful in the compositions of the invention is an amorphous water-insoluble hydrated compound of the formula $Na_x(yA1O_2.SiO_2)$, wherein x is a number from 1.0 to 1.2 and y is 1, said amorphous material being further characterized by a $Mg^{++}$ exchange capacity of from about 50 mg eq. $CaCO_3/g$. and a particle diameter of from about 0.01 micron to about 5 microns. This ion exchange builder is more fully described in British Patent No. 1,470,250.

A second water-insoluble synthetic aluminosilicate ion exchange material useful herein is crystalline in nature and has the formula $Na_z [(A1O_2)_y.(SiO_2)]xH_2O$, wherein z and y are integers of at least 6; the molar ratio of z and y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grams/gallon/minute/gram. These synthetic aluminosilicates are more fully described in British Patent No. 1,429,143.

In addition to the ingredients described hereinbefore, the preferred compositions herein frequently contain a series of optional ingredients which are used for the known functionality in conventional levels. While the detergent compositions are generally premised on aqueous, enzyme-containing detergent compositions, it is frequently desirable to use a phase regulant. This component together with water constitutes then the solvent matrix for the claimed liquid compositions. Suitable phase regulants are well-known in liquid detergent technology and, for example, can be represented by hydrotropes such as salts of alkylarylsulfonates having up to 3 carbon atoms in the alkyl group, e.g., sodium, potassium, ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 0 to 20%, the sum of phase regulant and water is normally in the range from 35% to 65%.

The preferred compositions herein can contain a series of further optional ingredients which are mostly used in additive levels, usually below about 5%. Examples of the like additives include: polyacids, suds regulants, opacifiers, antioxidants, bactericides, dyes, perfumes, brighteners and the like.

The beneficial utilization of the claimed compositions under various usage conditions can require the utilization of a suds regulant. While generally all detergents suds regulants can be utilized, preferred for use herein are alkylated polysiloxanes such as dimethylpolysiloxane, also frequently termed silicones. The silicones are frequently used in a level not exceeding 0.5%, most preferably between 0.01% and 0.2%.

It can also be desirable to utilize opacifiers inasmuch as they contribute to create a uniform appearance of the concentrated liquid detergent compositions. Examples of suitable opacifiers include: polystyrene commercially known as LYTRON 621 manufactured by Monsanto Chemical Corporation. The opacifiers are frequently used in an amount from 0.3% to 1.5%.

The compositions herein can also contain known antioxidants for their known utility, frequently radical scavengers in the art established levels, i.e., 0.001% to 0.25% (by reference to total composition). These antioxidants are frequently introduced in conjunction with fatty acids.

The liquid detergent compositions of the invention may also contain deflocculating polymers such as described in U.S. Ser. No. 664,513 to Kaiserman et al. filed Mar. 5, 1991 hereby incorporated by reference.

When the liquid composition is an aqueous composition, the balance of the formulation consists of an aqueous medium. When it is in the form of a non-aqueous composition, the above ingredients make up for the whole formulation (a non-aqueous composition may contain up to 5% water).

An ideal liquid detergent composition might contain (all percentages by weight):

(1) 5–70% detergent active;
(2) 0–50% builder;
(3) 0–40% electrolyte
(4) 0.01–5% enzyme;

(5) 0.1–15% enzyme stabilizer;

(6) 0–20% phase regulant; and (7) remainder water and minors

The detergent composition of the invention might also be a powdered detergent composition.

Such powdered compositions generally comprise from about 5–40% of a detergent active system which generally consists of an anionic, a nonionic active, a fatty acid soap or mixtures thereof; from 20–70% of an alkaline buffering agent; up to about 40% builder and balance minors and water.

The alkaline buffering agent may be any such agent capable of providing a 1% product solution with a pH of above 11.5 or even 12. Advantageous alkaline buffering agents are the alkali metal silicates, as they decrease the corrosion of metal parts in washing machines, and in particular sodium ortho meta- or di-silicates, of which sodium metasilicate is preferred. The alkaline buffering agent is present in an amount of from 0 to 70% by weight, preferably from 0 to 30% by weight.

In addition the compositions of the invention can and normally will contain detergency builders in an amount of up to 40% by weight and preferably from 5 to 25% by weight of the total composition.

Suitable builders include sodium, potassium and ammonium or substituted ammonium pyro- and tri-polyphosphates,-ethylene diamine tetraacetates, -nitrilotriacetates, -etherpolycarboxylates, -citrates, -carbonates, -orthophosphates, -carboxymethyloxysuccinates, etc. Other builders include DPA and ODS. Also less soluble builders may be included, such as e.g., an easily dispersible zeolite. Particularly preferred are the polyphosphate builder salts, nitrilotriacetates, citrates, carboxymethyloxysuccinates and mixtures thereof.

Other conventional materials may be present in minor amounts, provided they exhibit a good dissolving or dispersing behavior; for example sequestering agents, such as ethylenediamine tetraphosphonic acid; soil-suspending agents, such as sodium carboxymethylcellulose, polyvinylpyrrolidone or the maleic anhydride/vinylmethylether copolymer, hydrotropes; dyes; perfumes; optical brighteners; alkali-stable enzymes; germicides; anti-tarnishing agents; lather depressants; fabric softening agents; oxygen- or chlorine-liberating bleaches, such as dichlorocyanuric acid salts or alkalimetal hypochlorides.

The remainder of the composition is water, which is preferably present in hydrated form, such as e.g., in the form of silicate 5 aq.

An ideal powdered detergent composition might contain the following (all percentages by weight);

(10 5–40% detergent active;

(2) 0–40% builder;

(3) 0–30% buffer salt;

(4) 0–30 sulfate;

(5) 0–20% bleach system;

(6) 0-% enzyme; and (7) Minors plus water to 100%

The invention is set forth in greater detail in the examples which follow below. The examples are merely to illustrate the invention and are not intended to be limiting in any way.

EXAMPLE 1

Preparation of Sodium Lauryloxy (Ethoxy)$_n$ Acetyl Isethionate Via Directly Esterified Fatty Acid Isethionate (DEFI) Route A glass reactor consisting of a 500 ml cylindrical glass bottom piece and a 4-neck glass top piece which was fitted with a thermocouple, a mechanical stirrer, a nitrogen gas inlet tube and distillation apparatus were charged with 99.3 g (0.278 moles) of alkyl alkoxycarboxylic acid, 30.7 g (0.207 mole) sodium isethionate (that was predissolved in 54 mL of distilled, deionized (dd) water, and 0.1118% ZnO (0.1401 g). The vessel was heated using a heating mantle connected to a temperature controlled heating unit. At 45° C., the nitrogen sparging was initiated (40 cc/min), and the temperature stabilized at 103° C., until the water distilled off with small amount of alkoxy fatty acid. Once the water was removed, the reaction was heated to 220°– 240° C. for about 90 minutes. The reaction when cooled to room temperature was a brown viscous liquid. The reaction afforded 57.28% activity (70.57% yield) and 4.4% sodium isethionate. The semi-solid state was due to excess alkoxy fatty acid. Acetone washing removed the excess alkoxy fatty acid, and yielded a solid.

EXAMPLE 2

Preparation of Sodium Salt of Alkoxy Carboxylate 50 g (0.147 mole) of an alkyl alkoxy carboxylic acid ($C_{23}$ alkyl having average degree of ethoxylation of 2.5) and 500 mLs of dd water was placed in a 1 L Erlenmeyer flask equipped with a magnetic stir bar, pH electrode, on a magnetic stir plate. 154 g of 1N NaOH (0.154 mole) was added to raise the pH from 3 to 9.19. After clear solution was lyophilized, an off white solid was obtained.

EXAMPLE 3

Light Duty Liquid

A composition containing the following ingredients may be prepared.

| Component | % By Weight |
| --- | --- |
| Ammonium alkyl benzene sulfonate | 19.0 |
| Sodium lauryloxy (ethoxy)$_n$ acetyl isethionate | 11.0 |
| Lauric/myristic monoethanolamide | 3.0 |
| Sodium xylene sulfonate | 5.0 |
| Preservative, fragrance, dye and water | to 100% |

EXAMPLE 4

Hand or Body Cleanser

A composition containing the following ingredients may be prepared.

| Component | % By Weight |
| --- | --- |
| Sodium lauryloxy/myristyloxy (ethoxy)$_n$ acetyl isethionate | 13.0 |
| Coco amido propyl betaine | 4.5 |
| Carbopol 940* | 1.0 |

| Component | % By Weight |
|---|---|
| Laponite | 0.05 |
| Lauric/myristic acid | 5.6 |
| Sodium chloride | 2.8 |
| Preservative, fragrance, dye and water | to 100% |

*About 1% cross-linked polyacrylic acid having a molecular weight of about 4 million.

EXAMPLE 5

Toilet Bar Composition

A composition containing the following ingredients may be prepared:

| | |
|---|---|
| Sodium Cocoyloxy (2.5 EO) acetyl isethionate | 50% |
| Stearic Acid | 20% |
| Sodium Coco (2.5 EO) carboxylate | 7% |
| 82/18 Soap* | 4% |
| Sodium Isethionate | 4% |
| Coconut Fatty Acid | 3% |
| Sodium Stearate | 3% |
| Perfume | 1% |
| Water, preservatives & colorants | 5% |
| Organic and/or inorganic salts of the various ingredients | 3% |

*Ratio of coconut fatty acid to tallow fatty acid

EXAMPLE 6

In order to show that the isethionate esters of alkyl alkoxycarboxylic acid had advantageous physical properties, applicants compared the compounds of the invention where R is $C_{23}$ to a diethoxy isethionate compound as set forth in U.S. Ser. No. 08/045,951 filed Apr. 12, 1993, hereby incorporated by reference. The ethoxylated compounds of that reference have the formula:

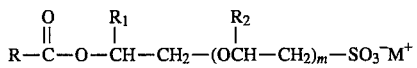

wherein R is an alkyl group having 8 to 18 carbons, m is an integer from 1 to 4, $R_1$ and $R_2$ are hydrogen or an alkyl group having 1 to 4 carbons and $M^+$ is a monovalent cation such as sodium, potassium or ammonium. Specifically, applicants have compared the compound of the invention where R is $C_{23}$ to ethoxylated sodium lauroyl diethoxy isethionate (SLDI).

As taught in U.S. Ser. No. 08/045,951 SLDI is a very good mild surfactant at least in that it foams better (using Ross-Miles test described herein) and dissolves less zein than the monoethoxylated sodium lauroyl isethionate (see Example 3 of that specification).

1. Foam Height

More specifically, foam is an important attribute in many consumer products (e.g., consumer products). Foam is one of the dominant factors that determines the commercial value of products such as shampoo, soap, etc. Also, acceptability of many consumer products is closely related to the quality and texture of the foam they produce (psychological aspect).

Since most of the foaming data on surfactants is typically obtained by the Ross-Miles method (Ross, J. and Miles, G. D., Am. Soc. For Testing Material Method D1173-53 Philadelphia, Pa. (1953); Oil & Soap (1958) 62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial foam height) and then again after a given amount of time (generally, 5 min).

Using this method, the foam height (measured initially) were reported for sodium lauroyl diethoxy isethionate (SLDI) and for a $C_{23}$ ester of the invention. All of the foaming was achieved at 45° C. in water with 120 ppm hardness. The foam height was represented in millimeters (mm).

Foam heights for the SLDI was 122 mm while heights for the $C_{23}$ ester of the invention was 163. Foam height for a nonethoxylated isethionate is negligible.

Zein Test

In Vitro "Mildness" Test
  Assessing Mildness

Many factors have been reported to have an influence on skin irritation such as removal of skin lipids, loss of naturally occurring hygroscopic materials in the stratum corneum, adsorption, protein denaturation, and epidermal lyposomal injury. Although there are many hypotheses regarding skin irritation, it is generally believed that surfactants become irritants because they penetrate the stratum corneum which is a "barrier" and then react with the inner cells of the epidermis.

Traditionally, the study of percutaneous absorption has focussed on measuring the diffusion of chemicals (e.g., surfactants through stratum corneum). Diffusion through an organ as complex as skin and its associated adnexal appendages is challenging to measure, much less to model. Another challenge of cutaneous metabolism is to assess the irritating potential, toxicity, and therapeutic potential of the penetrating compounds.

In vivo, the skin metabolism and percutaneous absorption are very difficult to measure. Finding adequate detection methods and setting up proper experiments are not easy tasks. In vitro studies however are used because of the simplicity of the experimental conditions.

We have obtained information on mildness potentials of the surfactant by carrying out in vitro tests which have been demonstrated to correlate well with in vivo tests.

In Vitro Zein Solubilization Test

Gotte (E. Gotte, Proc. Int. Cong. Surface Active Subs., 4th brussels (1964), 3, 83–90) and Schwinger (M. J. Schwinger, Kolloid-Z. Z. Poly., (1969), 233, 898) have shown that a surfactant's ability to solubilize zein, an insoluble maize protein, correlates well with surfactant irritation potential. Specifically, the lower the amount of zein protein dissolved, the milder a surfactant is. Conversely, the more zein dissolved, the more irritating the surfactant is.

In order to test irritancy potential, a 1% solution of surfactant (30 mL) was added to 1.5 g zein and stirred at room temperature for 1 hour. Residual zein was collected and dried to constant weight. Differences between starting and residual weights were used to calculate % zein dissolved.

The amount of zein dissolved using the surfactant of the invention (30%) was less than the amount dissolved using the already mild diethoxy material (35%). Given that sodium lauroyl monoethoxy isethionate dissolves 42% zein and sodium lauroyl isethionate dissolves 55% zein, it can be seen that the compound of this invention is extremely mild.

We claim:

1. A compound having the formula:

$$R(OC_mH_{m+1})_nOCH_2\overset{O}{\underset{\|}{C}}-\overset{X}{\underset{|}{O}}CH_2CH_2SO_3^-Na^+$$

wherein

R is a $C_8$ to $C_{24}$ alkyl or alkenyl group;

m is 1 to 3;

n is 1 to 5; and x is hydrogen or a $C_1$ to $C_3$ hydrocarbon.

2. A detergent or personal product composition comprising:

(1) 2 to 35% by weight of a surfactant selected from the group consisting of anionic surfactants other than (2) below; nonionic; cationic; ampholytic; and zwitterionic surfactants or mixtures thereof; and (2) a compound or mixture of compounds having the formula $$R(OC_mH_{m+1})_nOCH_2\overset{O}{\underset{\|}{C}}-\overset{X}{\underset{|}{O}}CH_2CH_2SO_3^-Na^+$$

wherein

R is a ($C_8$–$C_{24}$ alkyl or alkenyl group and wherein the value of R may vary within the mixture of compounds;

m is 1 to 3;

n is 1 to 5; and x is hydrogen or a $C_1$ to $C_3$ hydrocarbon.

3. A toilet bar composition comprising:

| | |
|---|---|
| Sodium Cocoyloxy (2.5 EO) acetyl isethionate | 50% |
| Stearic Acid | 20% |
| Sodium Coco (2.5 EO) carboxylate | 7% |
| 82/18 Soap* | 4% |
| Sodium Isethionate | 4% |
| Coconut Fatty Acid | 3% |
| Sodium Stearate | 3% |
| Perfume | 1% |
| Water, preservatives and colorant | 5% |
| Organic salts inorganic salts or mixtures thereof of ingredients not already in salt form | 3% |

*ratio of coconut fatty acid to tallow.

* * * * *

UNITED STATES PATENT AND TRADEMARK OFFICE
CERTIFICATE OF CORRECTION

PATENT NO. : 5,466,396
DATED : November 14, 1995
INVENTOR(S) : Madison et al.

It is certified that error appears in the above-indentified patent and that said Letters Patent is hereby corrected as shown below:

On the title page, column 1, change "Lever Brothers Company" to

— Lever Brothers Company, Division of Conopco, Inc.—

Signed and Sealed this

Twentieth Day of February, 1996

Attest:

BRUCE LEHMAN

Attesting Officer

Commissioner of Patents and Trademarks